United States Patent [19]

Farrell et al.

[11] 4,260,646
[45] Apr. 7, 1981

[54] METHOD FOR IDENTIFICATION OF ANIMALS

[75] Inventors: Beverly P. Farrell, P.O. Box 2250, College Station, Pullman, Wash. 99163; Michael E. Mucha, Albion, Wash.

[73] Assignee: Beverly P. Farrell, Pullman, Wash.

[21] Appl. No.: 86,592

[22] Filed: Oct. 19, 1979

[51] Int. Cl.³ .............................................. A61B 5/10
[52] U.S. Cl. .............................. 427/1; 264/DIG. 30; 427/4
[58] Field of Search ................ 427/1, 4; 264/DIG. 30

[56] References Cited

U.S. PATENT DOCUMENTS 2,313,807   3/1943   Curry ........................................ 427/1

Primary Examiner—Ronald H. Smith
Assistant Examiner—Janyce A. Bell
Attorney, Agent, or Firm—Wells, St. John & Roberts

[57] ABSTRACT

A technique for making a permanent imprint of trichoglyphs (cowlicks). A liquid solvent is applied to the surface of the trichoglyph. A flexible sheet of solvent-soluble material is pressed over the wetted trichoglyph area. The sheet is marked and indexed with respect to externally recognizable anatomical features of the animal adjacent to the trichoglyph area. This results in the impression of the trichoglyph configuration in geometric relation to indexed markings on the sheet indicative of the position of the trichoglyph on the body of the animal. The sheet is subsequently removed and dried. The resulting impression can be used to produce prints for later comparison purposes and for recording of the trichoglyph features.

13 Claims, 4 Drawing Figures ial being easily detected. Accurate animal identification has many uses, including health programs, proof of ownership, identification of stolen animals, issuance of certificates of registry, and in breeding programs.

METHOD FOR IDENTIFICATION OF ANIMALS

BACKGROUND OF THE INVENTION

This disclosure relates to a method for identifying individual animals. It is applicable to fur-bearing animals having distinctive trichoglyphs or cowlicks at identifiable positions on the body of the animal. While it will be described specifically in relation to identification of horses, it is to be understood that the disclosue is applicable to many other animals as well.

Reliable identification of animals assists in establishing proper health and animal care programs, issuance of regulatory certificates and accurate establishment of genetics-based breeding programs. Accurate identification also is important in proving ownership of the animal, in proving the nature of fraudulent markings applied to the animal, and in assisting the owner in claiming a stolen animal after it is recovered. In the particular case of animals having high monetary value, an identification system must further be unalterable, or must use identifying determinants which cannot be altered without the alteration being obvious.

While no single animal identification system is in itself perfect or totally reliable, there is need for a system having universal applicability, using visual markings which remain unchanged over the life of the animal and which makes alterations easily detectable.

The present description meets these standards by utilization of natural trichoglyphs or "cowlicks" as visual markings. An impression is made of at least one trichoglyph, and its location with respect to externally recognizable anatomical features of the animal is registered by markings provided on the impression as it is being made. The final impression can then be related to a grid indexed to identifiable features on the body of the horse. Significant features of the trichoglyph pattern can be plotted with respect to this grid to reduce identification of the trichoglyph pattern to a two dimensional mathematical statement for recording and data storage and retrieval at a later date.

Trichoglyphs are currently being used in at least two other species for identification. Zoologists at the U.S. Fish and Wildlife Service have studied the distribution of hairs in seals. It is reported that hair arrangement, size, and distribution are distinct for various genera of seals. With the skin fragments recovered from the stomachs of whales and sharks, investigators hope to identify which genus of seal is being preyed upon most heavily.

Even more interesting is the use of hair whorls for animal identification in the Far East. In the rice lands of Asia, the water buffalo is a valued beast of burden. They are treated with care and consideration. Religion and philosophy prohibit any form of animal identification that involves mutilation, and, therefore, tattooing and branding are not used. Until recently, traditional beliefs restricted the use of ear tags in livestock. In this part of the world the location of hair whorls are accepted as a means of livestock identification. It is reported that hair whorls are distinct for each individual water buffalo and have a legal basis for identification in Malaysia and the Philippines.

It is generaly agreed that hair slope and direction is determined in the early embryo. At this time, the individual hair is forming in the layer of skin termed the epidermis. To become fully developed, the hair must grow down to the underlying dermis and become anchored as the hair bulb. Concurrently, the underlying muscles and bones are growing and placing various planes of stretch on the skin. The plane of stretch will determine the direction of the hair. This theory proposed only recently with respect to the origin of hair whorls, explains why trichoglyphs are consistently seen in certain regions of the body.

One type of trichoglyph, the hair whorl, is created when the skin is stretched around prominences that occur in the early embryo. The frontal hair whorl on the head of the horse corresponds to the cowlick on the scalp of most people. The human embryo has a cranial dome around which the skin is stretched to produce the typical cowlick. In the developing equine embryo, there are several areas of the head that protrude to produce the frontal hair whorl. This variety in the shape of the skull of the early equine embryo results in the great many types of frontal whorls seen.

Once the trichoglyph is established, it is permanent and unalterable. This has been shown by experiments done on laboratory mice and guinea pigs in which surgical rotation of portions of skin did not alter original pattern or direction of the trichoglyph.

If one accepts the above theory as to development of trichoglyphs, it will be recognized that there is no primary genetic control of trichoglyphs, i.e., there are no genes that code for a specific type of trichoglyph. Therefore, one must conclude that the genetic make up of the animal determines its early embryonic form and the trichoglyphs that result are secondary to the stresses placed on the skin by the shape of the earyl embryo. Each trichoglyph is therefore unique to an individual animal.

The present disclosure is based upon the premise that a trichoglyph can serve as an accurate means for proving the identity of an animal. The use of trichoglyphs for identification purposes does away with the need for brands, lip tattoos and other markings which are sometimes objectionable as being cruel, unsightly and readily alterable.

Trichoglyphs are more reliable as visual determinants because of their permanence. Even surgical removal in the area of the trichoglyph leaves the surrounding hair pattern unchanged, making alterations easily detectable. A trichoglyph can be compared to fingerprints so far as visual determinants are concerned. In most cases, each is different. However, in the unlikely case of two animals having identical trichoglyphs, other characteristics such as age, color, size, markings and sex would no doubt differentiate the particular animals.

This disclosure is concerned with an effective system for recording the nature and accurate position of trichoglyphs for identification of an animal.

DESCRIPTION OF THE PREFERRED EMBODIMENT

Figure 1:
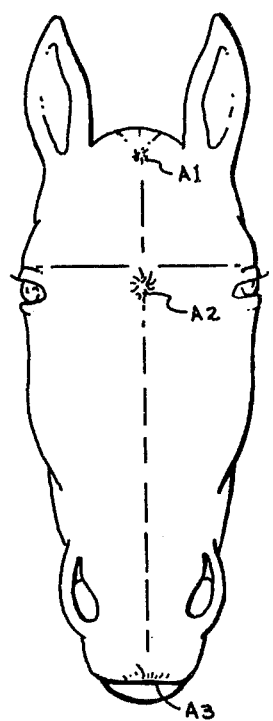
FIG. 1 is an illustration of the location of common trichoglyphs occurring in the head region of a horse.

This disclosure arose from a search for a method of animal identification that is unalterble without the alteration itself being obvious. It has been developed specifically for identification of horses, but is readily usable in the identification of other animals as well.

Classical methods of animal identification which have been used in the identification of horses include the recording of natural white marks, which can now be permanently added to by freeze marking techniques or eliminated temporarily by dyeing; recording of chestnuts, which are easily altered in shape and size by surgical means; and tattoos, which can be eliminated by laser beams of suitable wave length. Such alterations are not obvious to knowledgeable owners and, thus can lead to fraudulent practices.

When alteration of a trichoglyph is attempted by surgical removal of the vortical origin of a typical trichoglyph whorl, the surrounding hair continues to radiate from the center in the original manner. Similarly, attempts to transplant the vortical origin of a trichoglyph to another site with the possibility of establishing a new trichoglyph have always failed, and the resulting transplant has always been obvious.

Prior methods of animal identification utilizing trichoglyphs have been concerned only with their location. The purpose of this method is to provide an accurate means for recording the details of the trichoglyph and accurately defining its location on the animal. This information can subsequently be used for identification purposes, either as an exclusive identification system or in conjunction with one or more other natural or man-made identification systems.

Trichoglyphs are determined in the embryonic stage of development. They are caused by protuberances underlying the skin and stretching of the skin in a manner that gives a slant to the hair follicle. It appears that trichoglyph patterns are constant from birth until death and that location, as recorded on a young animal, can be interpolated by use of constants to determine location on the adult animal. Although there may be familial and breed tendencies, the pattern and location of whorls will prove to be unique to a given animal. It also appears practical to code trichoglyph patterns in a manner similar to that used for human fingerprints. Furthermore, the nature of trichoglyphs makes it possible to assign to them computer-compatible data that relates to their individual anatomical locations on the animal.

For identification purposes, an imprint or impression of a trichoglyph is made in a permanent manner such that it can be readily copied by photo mechanical transfer processes or photography methods. The imprint can be compared by direct overlay to a subsequently made imprint or can be compared by direct overlay to the animal itself.

The basic method involves the application of a liquid solvent material to the surface of the trichoglyph area to wet the hair contained within it. A solvent-soluble surface of a sheet of flexible material is pressed against the wetted trichoglyph area and held in place for a period of time adequate to enable the solvent to soften the surface of the sheet and make an impression of the trichoglyph area. The sheet is marked to indicate its position relative to externally recognizable anatomical features of the animal located adjacent to the trichoglyph area. The sheet of material is removed from contact with the animal and subsequently allowed to dry, thereby forming a permanent imprint or impression of the surface hairs within the trichoglyph itself.

When the impression is complete, grid lines or other reference indicia can be imprinted or overlaid on the imprint in registration with the marks indicative of the location of the trichoglyph on the body of the particular animal. The recogizable prominent portions or discernible features of the trichoglyph pattern can then be plotted with respect to these grid lines or indicia. Two dimensional measurements, whether along intersecting grid axes or radiating from one or more centers, can be used to mathematically define the locations of these prominent features. As will be recognized, such mathematical measurements are readily expressed as mathematical statements or data that can be stored and retrieved by use of a properly programmed computer.

Trichoglyphics in the Horse

Two generalizations can be made about the hair of the horse. In most instances, the individual hair shaft forms an acute angle with the surface of the skin. The chief exceptions to this rule are the hairs of the muzzle, eye, mane, and vortex of the hair whorls. Secondly, the direction of the hair is from the head toward the tail. Any disturbance in this tailward flow of hair results in a trichoglyph. The critical regions where trichoglyphs occur are numerous. They are seen in areas where hair streams are originating, colliding, or terminating.

For convenience of description, trichoglyphs are classified as one of five types: (1) whorls, (2) feathers, (3) crests, (4) stacks, and (5) multiple. Whorls are the most important trichoglyphic type. They are the origin of hair streams in a given region of the body. An example is the frontal whorl of the head, which will be discussed later. Whorls originate from a single point termed the "vortex." The central hairs of the vortex stand perpendicular to the surface of the skin. The hairs leave the vortex in a variety of patterns. A sunburst pattern occurs when the hairs radiate out in a direct line from the vortex. This differs markedly from the clockwise or counterclockwise patterns which often occur.

Whorls often give rise to a pattern termed feathering. These occur in the manner their name suggests. The hairs diverge in opposite directions along a central line. The central line may be linear or nonlinear. A prominent feather occurs consistently in the flank region. They often terminate as crests where they collide with hairs going the opposite direction. Crests are not considered primary trichoglyphs, but rather represent the termination of two or more hair streams. A trichoglyphic type of lesser importance is the stack. These are the opposite of whorls. They represent converging hair streams that terminate in a stack like arrangement. These are nondescript when they occur.

Combinations of any or all of the above types can occur at one site. The area where the mot combinations of trichoglyphic types occur is the region of the frontal hair whorl. The variety of trichoglyphs that occur in this area make it a valuable site for use in horse identification.

There are certain areas where trichoglyphs occur with a high degree of predictability. They have been described as occurring commonly in twenty three places with other rare ones found in some individuals. Briefly, the more common trichoglyphs occur in the region of the head, neck, and flank.

Location of Trichoglyphs

Figure 3:
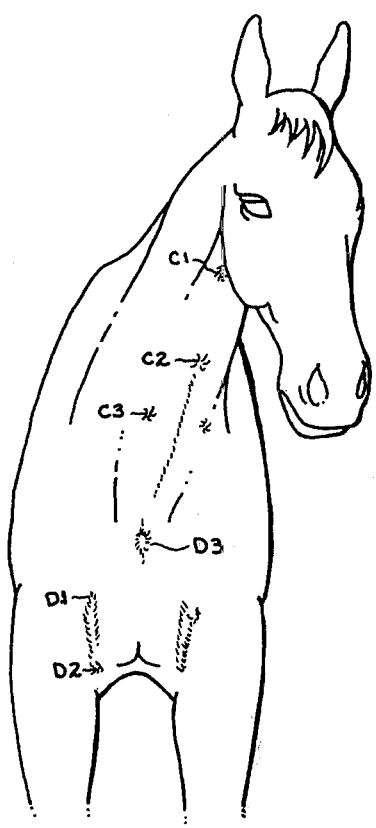
FIG. 3 is an illustration of common trichoglyphs occurring on the side of a horse.
Figure 2:
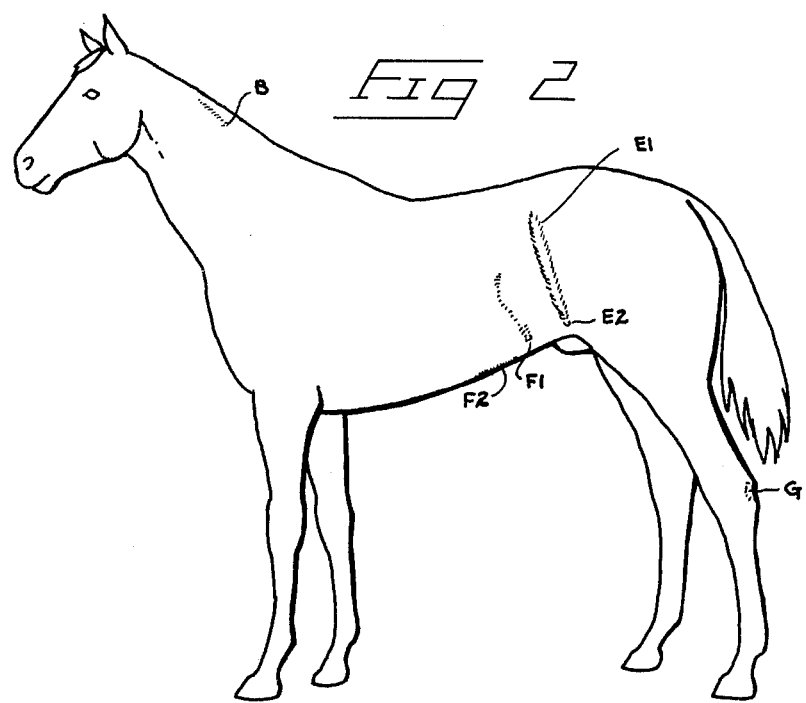
FIG. 2 is an illustration of common trichoglyphs occurring in the neck and pectoral regions of a horse.

FIGS. 1-3 illustrate common locations of cowlicks or trichoglyphs on the body of a horse. These patterns are provided only by way of a generalized example. They are identifiable by letters and numbers which relate to both the body region and location of each hair pattern. Similar charts can be readily drawn and identified with respect to other animals.

The present identification method has been primarily applied to the frontal trichoglyph on the head of a horse. Again, it will be evident that the same steps can be utilized in making imprints of any consistent body area bearing a trichoglyph.

FIG. 1 shows a frontal view of a horse's head, with reference lines relating to externally recognizable anatomical features. By drawing a transverse base line through the palpable dorsal limit of the bony orbits, there is a relatively even division of trichoglyphs above and below the line. For reference purposes, the transverse base line is intersected at its center by a vertical line over the fronal, parietal, and nasal sutures; palpable bony sutures that divde the horse verticaly into two equal halves Trichoglyph $A_1$ is located near the point of the forelock. It has always been observed as a stack.

Trichoglyph $A_2$ is located on the forehead in the general area of between the eyes. A horse may have one, two, three or four trichoglyphs in the $A_2$ category. $A_2$ trichoglyphs have, on rare occasions, been seen as short streams. When fraud is suspected, it has been helpful to take exact measurements from the base lines to the center of the cowlicks. The skin over the forehead is more adherent than elsewhere and is less likely to have great variation in measurement because of stretching of the skin.

Trichoglyph $A_3$ is located on the muzzle, but it is so sparsely haired that it may be difficult to see in the summer hair coat. Because of this, and because 100% of the horses have seemingly identical $A_3$ whorls, it is not considered of any value in differentiating horses. FIG. 1 shows trichoglyphs $A_1$, $A_2$, and $A_3$.

B trichoglyphs on the top of the neck (dorsal) are usually found in pairs, one on each side of the neck (FIG. 3). The B trichoglyphs frequently develop into streams. C trichoglyphs (FIG. 2) are found on the underside (ventral) of the neck. It has been reported that 99% of the horses have a cowlick in or within 10 centimeters of the throatlatch. In a few horses, probably less than 10%, two or three C trichoglyphs are found. These are usually all whorls, but some are large and can be quite showy. $C_2$ trichoglyph, located below the throatlatch, will often rotate inward.

$D_1$ and $D_2$ trichoglyphs form the top and bottom, respectively, of the paired streams on the chest (FIG. 2). These streams are usually well matched on a horse, but vary greatly between animals. Hairs spread out in a distinct fan at the top and bottom of the streams. An additional trichoglyph, $D_3$, often is found near the median line of the chest.

Trichoglyphs $E_1$ and $E_2$ are the top and bottom of what is commonly called the flank stream (FIG. 3). The right and left sides of the horse are well matched, but the position will vary between animals. A small percentage of horses will have two streams on one or both sides. The hair spreads into a distinct fan at the top of the stream where two hair flows meet.

Trichoglyph $F_1$ is a well-defined whorl that is found on each side of the abdomen. It is found on most horses. $F_2$, on the median line of the abdomen, is common in American breeds, but it is not recommended that it be used for identification because its observation may put the identifier in danger.

The G trichoglyph is found on the point of the hock or below on the rear of the cannon. It is found in less than 10% of the horses.

A variety of other trichoglyphs are rarely found but, if pressent, could present unique marks on individuals. If identical trichoglyphs are found on two horses, other characteristics such as age, color, height, white marks of signalment, and sex will help differentiate between the horses.

Trichoglyphs may follow familial patterns. For example, one family line of Morgan horses has a strong tendency to have two $A_2$ facial whorls.

While most trichoglyphs show the hair rotating outward, trichoglyph $C_2$ is rotated inward. Trihoglyhs $C_1$, $D_1$, $E_1$, and $E_2$ have fan-shaped hair arrangements.

If the center of a whorl is surgically removed, this will not confuse the total hair pattern. There is a distinct linear pattern radiating from whorls that extends out in all directions. If pieces of skin showing whorl patterns are transplanted to different sites, the alteration is obvious because of scar tissue and the interruption in hair flow patterns.

The Use of Trichoglyphics in Horse Identification

As mentioned earlier, the frontal whorl ($A_2$) appears to be a highly significant trichoglyph in terms of its origin for hair streams and its use in animal identification. It appears that the frontal whorl can satisfactorily serve as the sole identifying characteristic for an individual animal. To do this, it must fulfill important criteria. First, the frontal whorl must be unique for a given animal. Preliminary study suggests that even the most similar of whorls can be differentiated on close inspection.

Second, the whorl must demonstrate a high degree of variability in the population. This is definitely the case with the frontal whorl. The proposed classification scheme has a total of fifty five basic types (see table I). From the table it is evident that there is a high degree of variability in the type, number, and location of frontal whorls.

TABLE I

| Classification of the Frontal Hair Whorl | |
| --- | --- |
| I. Whorls - Without Feathers | 4. Oblique - Nonlinear |
| a. Starburst | A. Quadrant I |
| b. Clockwise | a. SB |
| c. Counterclockwise | b. CL |
| II. Whorl/Feather | c. CCL |
| 1. Dorsal Midline - Linear | B. Quadrant II |
| a. Starburst (SB) | C. Quadrant III |
| b. Clockwise (CL) | D. Quadrant IV |
| c. Counterclockwise (CCL) | III. Multiple |
| 2. Ventral Midline - Linear | 1. Double - Bilateral |
| a. SB | a. SB |
| b. CL | b. CL |
| c. CCL | c. CCL |
| 3. Oblique - Linear | d. Mixed |
| A. Quadrant I | 2. Double - Dorsal Ventral |
| a. SB | a. SB |
| b. CL | b. CL |
| c. CCL | c. CCL |
| B. Quadrant II | d. Mixed |
| C. Quadrant III | 3. Diagonal |
| D. Quadrant IV | a. SB |
| | b. CL |
| | c. CCL |
| | d. Mixed |

Third, an identifying characteristic must be unalterable. As is the case with finger prints in people, trichoglyphs in horses cannot be altered without being easily detected.

Fourth, current data storage systems require that information be transposable to paper and amenable to data retrieval. To meet this criteria, we have developed the present imprinting technique, from which a print of the frontal hair whorl can be made on paper. This process converts the hair whorl to a permanent record which can be filed as retrievable information. The process involves making an impression of the frontal hair whorl. The relatively flat surface of the horse's head lends itself nicely to this step. A positive duplicate of the imprint can be made by conventional photographic processes.

This technique is quick and convenient. It is well tolerated by the horse and owner since it is noninvasive and leaves no permanent mark. Most important, the imprints have a high degree of repeatability. When subsequent imprints have been taken of the same horse at a later date, they have been found to be nearly identical.

Details of the Method

The process consists of thoroughly cleaning the area of the frontal whorl, and moistening the hair with a special solvent. A clear, square piece of plastic 20 (FIG. 4) is placed on the whorl at a specific location which relates to certain anatomical sites on the horse. If need be, prints can be repeated at a later date and placed at the exact location of the first print. The impression left on the print should be identical to the pattern of the second, third or fourth print. Next, pressure is applied to the sheet of plastic, and the solvent causes the film to melt and trace the hair pattern. After carefully removing the plastic, it will dry to form a three-dimensional imprint of the whorl.

In making the imprint, it is necessary to relate the sheet of material to the anatomical sites on the horse adjacent to the trichoglyph. We use a simple combination of perpendicular transverse and upright lines visible in the illustration shown in FIG. 1, as well as on the imprint shown in FIG. 4. The transverse line 10 is established on the animal between the palpable supraorbital foramina. The upright line 11 is established mid sagitally through the parietel crest and the frontal and nasal sutures. The location of the $A_2$ trichoglyph is generally in the area of intersection of these two lines.

Figure 4:
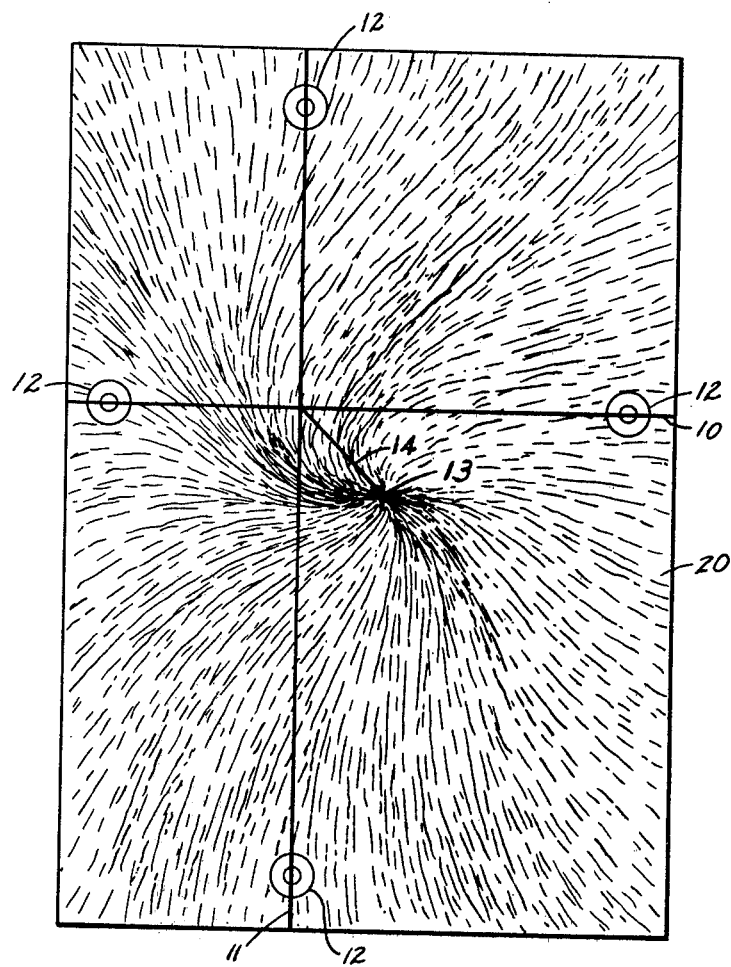
FIG. 4 is an illustration of a trichoglyph impression, showing the addition of a grid and plotting line.

To make an imprint, we are now using a system whereby the supraorbital foramina are palpated, and a small marker is affixed over each foramen. In a similar manner, the frontal suture is palpated and marked at a spot high on the cranium, and the nasal suture is located and marked at a lower spot on the face. Any three of these marks are sufficient to establish the location of the supraorbital foramina and the mid-saggital line on the imprint. The imprint materials are a sheet 20 of clear, flexible, solvent-soluble plastic and a liquid solvent that affects the plastic. Specifically, we use an acetate sheet and acetone. After a good brushing to clean away all debris, the trichoglyph and surrounding hair are wetted with acetone, and the acetate sheet is pressed onto the hair. The acetate sheet is removed, and in a few minutes it is dry. When the sheet is dry, the trichoglyph pattern is stable. The imprint shows minute details of hair flow pattern (FIG. 4).

The markers, which leave an imprint shown at 12 (FIG. 4) can comprise any three dimensional element which is inert with respect to the liquid solvent and which can be applied or attached to the surface of the trichoglyph area. As a simple example, the imprint shown in FIG. 4 was made after first attaching to the surface of the trichoglyph four adhesive reinforcement rings of the type used in ring binder notebooks. The particular nature of the markers is not critical to the invention, so long as they produce visible impressions or marks on the sheet of material after the step of pressing it against the wetted external surface of the trichoglyph area.

As an alternative, premarked sheets of plastic film could be placed over the trichoglyph area to make the impression, each sheet being indexed with respect to the anatomical features of the animal during placement. Markings might also be applied externally during the time the sheet is pressed against the surface of the animal.

The completed three-dimensional trichoglyph impression shows the $A_2$ whorl or whorls. The four small markers are recorded as voids in the hair flow pattern. The total imprint is then divided into quadrants by scribing a transverse line between the two marks representing the supraorbital foramina and a mid-saggital line between the two reference points on the frontal and nasal sutures. The exact location of the vortical origin of the trichoglyph(s) can then be plotted from the spot where these two lines intersect like nautical navigation dealing with relative positions of ships at sea. We can specify the bearing from this point through 360° (assume the mark on the frontal suture is true north/south). The range is given as millimeters instead of nautical miles. We have also used a grid pattern of location.

FIG. 4 illustrates a print of a trichoglyph made from an impression according to this method. The numeral 13 identifies the center of vortex of a typical whorl. Line 14 radiates from the intersection of lines 10 and 11. The angular position of this line can be readily described with respect to the intersecting reference lines. The distance along line 14 from the intersection of lines 10 and 11 to the vortex 13 can be readily measured and recorded. Similarly, the position of the vortex can be mathematically described on the perpendicular grid defined by the lines 10, 11. The methods of measurement and recording necessary to mathematically describe the locations of prominent features in the trichoglyph are believed to be evident to those skilled in this field. Similarly, such mathematical relationships can be readily transferred into data which is capable of being stored in the memory of a computer for future reference and retrieval.

The trichoglyph imprint process is capable of widespread use in the identification of many types of animals. It should serve the purpose of positive identification for many purposes, including selective breeding, disease control, proof of ownership, and proof or fraudulent identification. The transparent trichoglyph imprint can be superimpose over the trichoglyph at any future time to prove identity, or descriptive terminology can be generated.

While the specific system described herein has been found most practical by use of acetone as the liquid solvent and a transparent sheet of acetate as the plastic film, it is to be understood that other solvents and corresponding sheet materials which are non-injurious to the animal can be substituted in place of these specific materials.

Having described our invention, we claim:

1. A method of recording identifying features of an animal bearing a trichoglyph area adjacent externally recognizable anatomical features, comprising the following steps:
   applying to the surface of the trichoglyph are a liquid solvent material that is non-injurious to the animal, to wet the hair contained therein;
   pressing a solvent-soluble surface of a sheet of flexible material against the wetted hair in the trichoglyph area over a period of time adequate to enable the solvent to soften the surface of the sheet and make an impression thereon;
   marking the sheet about said surface to indicate its position relative to externally recognizable anatomical features of the animal located adjacent to the trichoglyph area;
   moving the sheet of flexible material from contact with the animal; and
   permitting the solvent-soluble surface of the sheet of flexible material to dry.

2. A method as set out in claim 1 wherein the step marking the sheet comprises the following substeps:
   attaching a three dimensional element to the trichoglyph area of the animal in geometric registration with at least one adjacent anatomical feature, the element having an external surface area which is inert to the solvent and having a relatively small area in relation to the trichoglyph area; and
   wetting the external surface of the element with the liquid solvent during the application of solvent to the surface of the trichoglyph area;
   whereby the step of pressing the solvent-soluble surface of the sheet against the wetted external surface of the trichoglyph area also results in the production of an impression of the element and its position within the trichoglyph area.

3. A method as set out in claim 1 wherein the step of marking the sheet comprises the following substeps:
   attaching two or more three dimensional elements to the trichoglyph area of the animal in geometric registration with at least one adjacent anatomical feature, the elements each having individual external surfaces inert relative to the solvent and having a relatively small area in relation to the trichoglyph area; and
   wetting the external surfaces of the elements while applying the liquid solvent to the surface of the trichoglyph area;
   whereby the step of pressing the solvent-soluble surface of the sheet against the wetted external surface of the trichoglyph area also results in the production of an impression of the external surfaces of the elements and their respective positions within the trichoglyph area.

4. A method as set out in claim 1 comprising the following additional step:
   subsequently drawing grid lines across said sheet in registration with the resulting marks indicative of the position of the sheet relative to the recognizable external anatomical features of the animal during making of the impression.

5. A method as set out in claim 1 wherein the sheet is comprised of transparent plastic material.

6. A method as set out in claim 1 wherein the sheet is comprised of transparent acetate film, and wherein the liquid solvent comprises acetone.

7. A method as set out in claim 1 comprising the following additional step:
   mathematically plotting the vortices within the impression of the trichoglyph area with respect to the resulting marks indicative of the position of the sheet relative to the recognizable external anatomical features of the animal during production of the impression.

8. A method of recording identifying features of an animal having a frontal trichoglyph area on its head, comprising the following steps:
   wetting the hair located within the frontal trichoglyph area by application of a liquid solvent material that is non-injurious to the animal and inert to the hair and skin surfaces of the animal;
   pressing a solvent-soluble surface of a sheet of flexible material against the wetted hair in the trichoglyph area over a period of time adequate to enable the solvent to soften the surface of the sheet and make an impression thereon of the hair patterns within the trichoglyph area;
   marking the sheet about said surface to indicate its position relative to anatomical features of the head located adjacent to the trichoglyph area;
   removing the sheet of flexible material from contact with the animal; and
   permitting the solvent-soluble surface of the sheet of flexible material to dry.

9. A method as set out in claim 8 comprising the following additional step:
   subsequently drawing grid lines across said sheet in registration with the resulting marks indicative of the position of the sheet relative to the anatomical features of the head.

10. A method as set out in claim 8 wherein the sheet is comprised of transparent material.

11. A method as set out in claim 8 wherein the sheet is comprised of transparent acetate film, and wherein the liquid solvent comprises acetone.

12. A method as set out in claim 8 comprising the following additional step:
    mathematically plotting discernible features of the hair pattern within the impression of the trichoglyph area with respect to the resulting marks indicative of the position of the sheet relative to the anatomical features of the head.

13. A method as set out in claim 8 wherein the step of marking the sheet comprises the following substeps:
    attaching two or more three dimensional elements to the trichoglyph area on the head of the animal in geometric registration with at least one anatomical feature adjacent to such area, the elements having individual external surfaces inert relative to the solvent and having a relatively small area in relation to the trichoglyph area; and
    wetting the external surfaces of the elements while applying the liquid solvent to the surface of the trichoglyph area;
    whereby the step of pressing the solvent-soluble surface of the sheet against the wetted external surface of the trichoglyph area also results in the production of an impression of the elements and their respective positions within the trichoglyph area.

* * * * *